(12) United States Patent
Zubok et al.

(10) Patent No.: US 9,132,020 B2
(45) Date of Patent: *Sep. 15, 2015

(54) WEDGE RAMP DISTRACTOR FOR USE IN IMPLANTING ARTIFICIAL INTERVERTEBRAL DISCS

(75) Inventors: Rafail Zubok, Midland Park, NJ (US); Michael W. Dudasik, Nutley, NJ (US); Thomas J. Errico, Summit, NJ (US)

(73) Assignee: SpineCore, Inc., Allendale, NJ (US)

( * ) Notice: Subject to any disclaimer, the term of this patent is extended or adjusted under 35 U.S.C. 154(b) by 727 days.

This patent is subject to a terminal disclaimer.

(21) Appl. No.: 12/501,889

(22) Filed: Jul. 13, 2009

(65) Prior Publication Data
US 2009/0312765 A1      Dec. 17, 2009

Related U.S. Application Data

(63) Continuation of application No. 10/782,981, filed on Feb. 20, 2004, now Pat. No. 7,575,576, which is a continuation-in-part of application No. 10/425,267, filed on Apr. 29, 2003, now Pat. No. 7,235,081, which (Continued)

(51) Int. Cl.
*A61B 17/60*     (2006.01)
*A61F 2/44*      (2006.01)
(Continued)

(52) U.S. Cl.
CPC ............. *A61F 2/442* (2013.01); *A61F 2/446* (2013.01); *A61F 2/4425* (2013.01); *A61F 2/4611* (2013.01); *A61F 2/4684* (2013.01);
(Continued)

(58) Field of Classification Search
CPC ............ A61F 2/4611; A61B 2017/0256

USPC ........................................ 606/86 A, 90, 99
See application file for complete search history.

(56) References Cited

U.S. PATENT DOCUMENTS 786,844 A    4/1905  Sanders
801,151 A    10/1905 McKeever et al.
(Continued)

FOREIGN PATENT DOCUMENTS

DE    3023942       1/1982
EP    0369603 A1    5/1990
(Continued)

OTHER PUBLICATIONS

Surgical Technique Using FRA Spacer Instruments, Technique Guide, Synthes Spine, 1998.

*Primary Examiner* — Brian Pellegrino
(74) *Attorney, Agent, or Firm* — Lerner, David, Littenberg, Krumholz & Mentlik, LLP

(57) ABSTRACT

Instruments and methods for distracting an intervertebral space and inserting and impacting artificial intervertebral discs. A wedge distractor employing opposing ramps through which an inserter/impactor holding an artificial intervertebral disc is admitted, the passage of which through the distractor results in distraction of the intervertebral space simultaneous with insertion of the artificial intervertebral disc. A method of distracting an intervertebral space comprising the steps of inserting a distractor having opposing ramped surfaces into an intervertebral space and inserting an inserter/impactor holding an artificial intervertebral disc between the opposing ramped surfaces of the distractor to insert/impact the artificial intervertebral disc in the intervertebral space. A system for distracting an intervertebral space employing a wedge distractor, inserter/impactor and artificial intervertebral implant.

4 Claims, 12 Drawing Sheets

Related U.S. Application Data is a continuation-in-part of application No. 10/282,356, filed on Oct. 29, 2002, now Pat. No. 7,169,182, which is a continuation-in-part of application No. 10/256,160, filed on Sep. 26, 2002, now Pat. No. 6,989,032, which is a continuation-in-part of application No. 10/175,417, filed on Jun. 19, 2002, now Pat. No. 7,563,285, which is a continuation-in-part of application No. 10/151,280, filed on May 20, 2002, now Pat. No. 7,604,664, which is a continuation-in-part of application No. 09/970,479, filed on Oct. 4, 2001, now Pat. No. 6,669,730, which is a continuation-in-part of application No. 09/968,046, filed on Oct. 1, 2001, now abandoned, said application No. 10/151,280 is a continuation-in-part of application No. 10/140,153, filed on May 7, 2002, now abandoned, which is a continuation-in-part of application No. 09/970,479, filed on Oct. 4, 2001, now Pat. No. 6,669,730, and a continuation-in-part of application No. 10/128,619, filed on Apr. 23, 2002, now Pat. No. 6,863,689, which is a continuation-in-part of application No. 09/906,119, filed on Jul. 16, 2001, now Pat. No. 6,607,559, and a continuation-in-part of application No. 09/982,148, filed on Oct. 18, 2001, now Pat. No. 6,673,113.

(51) Int. Cl.
*A61F 2/46* (2006.01)
*A61B 17/02* (2006.01)
*A61F 2/30* (2006.01)

(52) U.S. Cl.
CPC ..... *A61B2017/0256* (2013.01); *A61F 2/30742* (2013.01); *A61F 2/30767* (2013.01); *A61F 2002/302* (2013.01); *A61F 2002/3092* (2013.01); *A61F 2002/30171* (2013.01); *A61F 2002/30187* (2013.01); *A61F 2002/30331* (2013.01); *A61F 2002/30365* (2013.01); *A61F 2002/30378* (2013.01); *A61F 2002/30433* (2013.01); *A61F 2002/30441* (2013.01); *A61F 2002/30443* (2013.01); *A61F 2002/30444* (2013.01); *A61F 2002/30446* (2013.01); *A61F 2002/30451* (2013.01); *A61F 2002/30454* (2013.01); *A61F 2002/30492* (2013.01); *A61F 2002/30502* (2013.01); *A61F 2002/30507* (2013.01); *A61F 2002/30518* (2013.01); *A61F 2002/30528* (2013.01); *A61F 2002/30538* (2013.01); *A61F 2002/30563* (2013.01); *A61F 2002/30565* (2013.01); *A61F 2002/30571* (2013.01); *A61F 2002/30594* (2013.01); *A61F 2002/30604* (2013.01); *A61F 2002/30649* (2013.01); *A61F 2002/30662* (2013.01); *A61F 2002/30769* (2013.01); *A61F 2002/30772* (2013.01); *A61F 2002/30774* (2013.01); *A61F 2002/30785* (2013.01); *A61F 2002/30841* (2013.01); *A61F 2002/30909* (2013.01); *A61F 2002/30975* (2013.01); *A61F 2002/443* (2013.01); *A61F 2002/4619* (2013.01); *A61F 2002/4627* (2013.01); *A61F 2002/4628* (2013.01); *A61F 2220/0025* (2013.01); *A61F 2220/0033* (2013.01); *A61F 2220/0041* (2013.01); *A61F 2220/0058* (2013.01); *A61F 2230/005* (2013.01); *A61F 2230/0034* (2013.01); *A61F 2230/0065* (2013.01); *A61F 2250/0006* (2013.01); *A61F 2310/00017* (2013.01); *A61F 2310/00023* (2013.01); *A61F 2310/00365* (2013.01)

(56) References Cited

U.S. PATENT DOCUMENTS

| | | |
|---|---|---|
| 856,660 A | 6/1907 | Schall et al. |
| 1,099,811 A | 6/1914 | Moise et al. |
| 1,117,562 A | 11/1914 | Hale |
| 1,243,860 A | 10/1917 | Olson et al. |
| 1,425,845 A | 8/1922 | Foster |
| 1,542,123 A | 6/1925 | Eifel |
| 1,882,462 A | 10/1932 | Weber |
| 2,167,599 A | 7/1939 | Yanits |
| 2,243,305 A | 5/1941 | Adler |
| 2,546,287 A | 3/1951 | Zelgert |
| 2,625,848 A | 1/1953 | Davies et al. |
| 3,029,670 A | 4/1962 | Over et al. |
| 4,820,305 A | 4/1989 | Harms et al. |
| 4,903,692 A | 2/1990 | Reese |
| 4,968,010 A | 11/1990 | Odobasic |
| 4,997,432 A | 3/1991 | Keller et al. |
| 5,015,247 A | 5/1991 | Michelson |
| 5,026,373 A | 6/1991 | Ray et al. |
| 5,122,130 A * | 6/1992 | Keller .................. 606/86 A |
| 5,306,309 A | 4/1994 | Wagner et al. |
| 5,370,697 A | 12/1994 | Baumgartner |
| 5,571,109 A | 11/1996 | Bertagnoli et al. |
| 5,658,337 A | 8/1997 | Kohrs et al. |
| 5,667,347 A | 9/1997 | Matthews |
| 5,683,399 A | 11/1997 | Jones |
| 5,749,916 A | 5/1998 | Richelsoph |
| 5,755,798 A | 5/1998 | Papavero et al. |
| 5,766,252 A | 6/1998 | Henry et al. |
| 5,893,889 A | 4/1999 | Harrington |
| 6,015,436 A | 1/2000 | Schonhoffer |
| 6,063,088 A | 5/2000 | Winslow |
| 6,159,211 A | 12/2000 | Boriani et al. |
| 6,159,215 A | 12/2000 | Urbahns et al. |
| 6,261,296 B1 | 7/2001 | Aebi et al. |
| 6,391,058 B1 | 5/2002 | Kuslich et al. |
| 6,402,785 B1 | 6/2002 | Zdeblick et al. |
| 6,440,133 B1 | 8/2002 | Beale et al. |
| 6,471,725 B1 | 10/2002 | Ralph et al. |
| 6,514,256 B2 | 2/2003 | Zucherman et al. |
| 6,558,387 B2 | 5/2003 | Errico et al. |
| 6,582,431 B1 | 6/2003 | Ray |
| 6,582,451 B1 | 6/2003 | Marucci et al. |
| 6,599,291 B1 | 7/2003 | Foley et al. |
| 6,652,533 B2 | 11/2003 | O'Neil |
| 6,723,127 B2 | 4/2004 | Ralph et al. |
| 6,733,532 B1 | 5/2004 | Gauchet et al. |
| 6,887,274 B2 | 5/2005 | Ralph et al. |
| 6,989,032 B2 | 1/2006 | Errico et al. |
| 7,011,684 B2 | 3/2006 | Eckman |
| 7,025,787 B2 | 4/2006 | Bryan et al. |
| 7,048,764 B2 | 5/2006 | Ferree |
| 7,060,099 B2 | 6/2006 | Carli et al. |
| 7,066,959 B2 | 6/2006 | Errico et al. |
| 7,083,651 B2 | 8/2006 | Diaz et al. |
| 7,118,580 B1 | 10/2006 | Beyersdorff et al. |
| 7,122,055 B2 | 10/2006 | Ralph et al. |
| 7,160,327 B2 | 1/2007 | Errico et al. |
| 7,169,182 B2 | 1/2007 | Errico et al. |
| 7,214,244 B2 | 5/2007 | Zubok et al. |
| 7,235,081 B2 | 6/2007 | Errico et al. |
| 7,326,216 B2 | 2/2008 | Bertagnoli et al. |
| 7,326,250 B2 | 2/2008 | Beaurain et al. |
| 7,491,241 B2 | 2/2009 | Errico et al. |
| 7,575,576 B2 * | 8/2009 | Zubok et al. ............. 606/86 A |
| 7,635,368 B2 | 12/2009 | Errico et al. |
| 7,713,302 B2 | 5/2010 | Ralph et al. |
| 2001/0016773 A1 | 8/2001 | Serhan et al. |
| 2001/0039452 A1 | 11/2001 | Zucherman et al. |
| 2002/0082597 A1 | 6/2002 | Fraser |
| 2002/0111681 A1 | 8/2002 | Ralph et al. |

(56) References Cited

U.S. PATENT DOCUMENTS

| | | |
|---|---|---|
| 2002/0111683 A1 | 8/2002 | Ralph et al. |
| 2002/0111684 A1 | 8/2002 | Ralph et al. |
| 2002/0128714 A1 | 9/2002 | Manasas et al. |
| 2002/0193880 A1 | 12/2002 | Fraser |
| 2003/0009223 A1 | 1/2003 | Fehling et al. |
| 2003/0009224 A1 | 1/2003 | Kuras |
| 2003/0014111 A1 | 1/2003 | Ralph et al. |
| 2003/0023306 A1 | 1/2003 | Liu et al. |
| 2003/0040801 A1 | 2/2003 | Ralph et al. |
| 2003/0045939 A1 | 3/2003 | Casutt |
| 2003/0069586 A1 | 4/2003 | Errico et al. |
| 2003/0074067 A1 | 4/2003 | Errico et al. |
| 2003/0078662 A1 | 4/2003 | Ralph et al. |
| 2003/0078666 A1 | 4/2003 | Ralph et al. |
| 2003/0078667 A1 | 4/2003 | Manasas et al. |
| 2003/0083749 A1 | 5/2003 | Kuslich et al. |
| 2003/0100951 A1 | 5/2003 | Serhan et al. |
| 2003/0135278 A1 | 7/2003 | Eckman |
| 2003/0187508 A1 | 10/2003 | Cauthen |
| 2003/0191533 A1 | 10/2003 | Dixon et al. |
| 2003/0191534 A1 | 10/2003 | Viart et al. |
| 2003/0195514 A1 | 10/2003 | Trieu et al. |
| 2003/0208271 A1 | 11/2003 | Kuras |
| 2003/0208273 A1 | 11/2003 | Eisermann et al. |
| 2003/0229358 A1 | 12/2003 | Errico et al. |
| 2004/0204762 A1 | 10/2004 | Ralph et al. |
| 2004/0267276 A1 * | 12/2004 | Camino et al. ................ 606/99 |
| 2005/0119665 A1 | 6/2005 | Keller |
| 2005/0131542 A1 | 6/2005 | Benzel et al. |
| 2005/0177171 A1 | 8/2005 | Wetzler et al. |
| 2007/0016221 A1 | 1/2007 | Beyersdorff et al. |
| 2007/0198092 A1 | 8/2007 | Errico et al. |

FOREIGN PATENT DOCUMENTS

| | | |
|---|---|---|
| EP | 1219266 | 7/2002 |
| WO | 91/13598 | 9/1991 |
| WO | 9929271 A1 | 6/1999 |

* cited by examiner (Section C-C on Fig. 1i)

(Perspective of Fig. 1h)

(Section A-A on Fig. 1g)

(Section B-B on Fig. 1g)

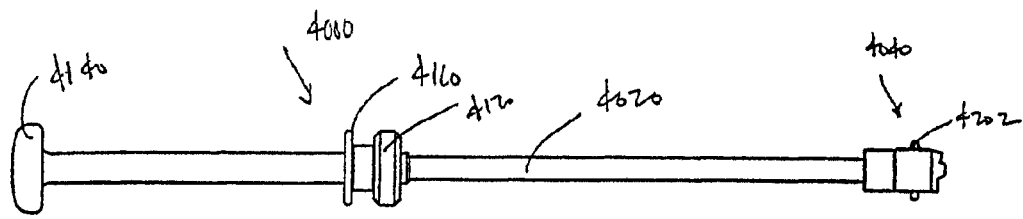
FIG. 2a
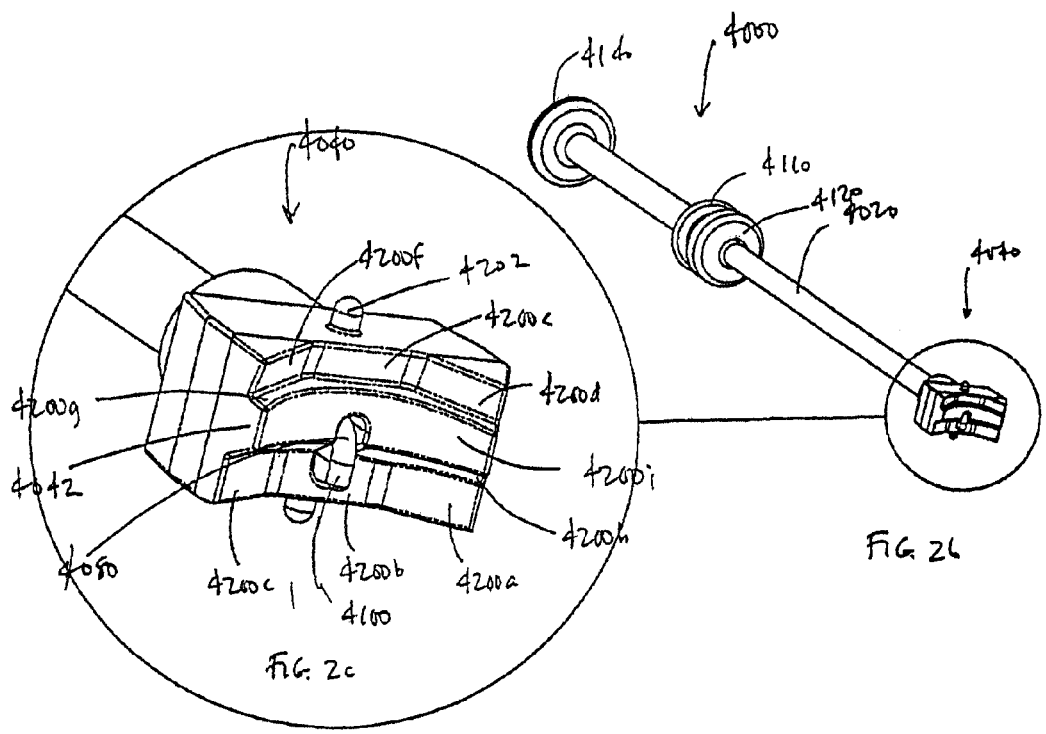
FIG. 2c
FIG. 2b

WEDGE RAMP DISTRACTOR FOR USE IN IMPLANTING ARTIFICIAL INTERVERTEBRAL DISCS

CROSS-REFERENCE TO RELATED APPLICATIONS

The present application is a continuation application of U.S. patent application Ser. No. 10/782,981 (filed on Feb. 20, 2004) entitled "Wedge Ramp Distractor for use in Implanting Artificial Intervertebral Discs", which is a continuation-in-part application of U.S. patent application Ser. No. 10/425,267 (filed Apr. 29, 2003) entitled "Wedge Plate Inserter/Impactor and Related Methods for Use in Implanting an Artificial Intervertebral Disc", now U.S. Pat. No. 7,235,081 ("the '081 patent"), which is a continuation-in-part application of U.S. patent application Ser. No. 10/282,356 (filed Oct. 29, 2002) entitled "Instrumentation and Methods For Use In Implanting an Artificial Intervertebral Disc", now U.S. Pat. No. 7,169,182 ("the '182 patent"), which is a continuation-in-part application of U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post", now U.S. Pat. No. 6,989,032 ("the '032 patent"), which is a continuation-in-part application of U.S. patent application Ser. No. 10/175,417 (filed Jun. 19, 2002) entitled "Artificial Intervertebral Disc Utilizing a Ball Joint Coupling", which is a continuation-in-part application of U.S. patent application Ser. No. 10/151,280 (filed May 20, 2002) entitled "Tension Bearing Artificial Disc Providing a Centroid of Motion Centrally Located Within an Intervertebral Space", which is a continuation-in-part application of both U.S. patent applications Ser. No. 09/970,479 (filed Oct. 4, 2001) entitled "Intervertebral Spacer Device Utilizing a Spirally Slotted Belleville Washer Having Radially Extending Grooves", now U.S. Pat. No. 6,669,730 ("the '730 patent") as well as U.S. patent application Ser. No. 10/140,153 (filed May 7, 2002) entitled "Artificial Intervertebral Disc Having a Flexible Wire Mesh Vertebral Body Contact Element" now abandoned, the '730 patent being a continuation-in-part application of U.S. patent application Ser. No. 09/968,046 (filed Oct. 1, 2001) entitled "Intervertebral Spacer Device Utilizing a Belleville Washer Having Radially Extending Grooves", now abandoned, and U.S. patent application Ser. No. 10/140,153 being a continuation-in-part application of both U.S. patent application Ser. No. 09/970,479 (filed Oct. 4, 2001) entitled "Intervertebral Spacer Device Utilizing a Spirally Slotted Belleville Washer Having Radially Extending Grooves", now U.S. Pat. No. 6,669,730 ("the '730 patent") as well as U.S. patent application Ser. No. 10/128,619 (filed Apr. 23, 2002) entitled "Intervertebral Spacer Having a Flexible Wire Mesh Vertebral Body Contact Element", now U.S. Pat. No. 6,863,689 ("the '689 patent") which is a continuation-in-part application of both U.S. patent application Ser. No. 09/906,119 (filed Jul. 16, 2001) entitled "Trial Intervertebral Distraction Spacers", now U.S. Pat. No. 6,607,559 ("the '559 patent") as well as U.S. patent application Ser. No. 09/982,148 (filed Oct. 18, 2001) entitled "Intervertebral Spacer Device Having Arch Shaped Spring Elements", now U.S. Pat. No. 6,673,113 ("the '113 patent"). All of the above mentioned applications are hereby incorporated by reference herein in their respective entireties.

FIELD OF THE INVENTION

This invention relates generally to systems and methods for use in spine arthroplasty, and more specifically to instruments for distracting an intervertebral space and inserting and impacting artificial intervertebral discs, and methods of use thereof.

BACKGROUND OF THE INVENTION

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column. More recently, the development of non-fusion implant devices, which purport to permit continued natural movement in the tri-joint complex, have provided great promise as a preferably alternative to fusion devices. The region of the back that needs to be corrected, as well as the individual variations in anatomy, determine the appropriate surgical protocol and implantation assembly. Generally, the preparation of the intervertebral space for the receipt of fusion or non-fusion devices involves removing the damaged disc material and thereafter distracting the adjacent vertebral bones to their appropriate distance apart. Once the proper height of the intervertebral space is restored, the fusion or non-fusion device can be implanted.

It is an object of the invention to provide instrumentation and methods that enable surgeons to more accurately, easily, and efficiently implant fusion or non-fusion devices. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes, among other aspects, an inserter/impactor (sometimes referred to herein as an "inserter/impactor") useful for holding and manipulating artificial intervertebral discs, a wedge-ramp distractor, and a parallel insertion distractor, the latter two items being useful for distracting an intervertebral space and inserting an artificial intervertebral disc therein.

More particularly, the systems and methods disclosed herein are intended for use in spine arthroplasty procedures, and specifically for use with the systems and methods described herein in conjunction with the systems and methods in conjunction with the systems and methods described in U.S. patent application Ser. No. 10/282,356 (filed Oct. 29, 2002) entitled "Instrumentation and Methods For Use In Implanting an Artificial Intervertebral Disc" (hereinafter referred to as "the '356 application") as well as U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post" (hereinafter referred to as "the '160 application") as well as U.S. patent application Ser. No. 09/906,127 (filed Jul. 16, 2001) entitled "Insertion Tool For Use With Intervertebral Spacers", the entirety of which is incorporated by reference herein (hereinafter referred to as "the '127 application"). However, it should be understood that the systems and methods described herein are also suitable for use with other systems and methods without departing from the scope of the invention.

While the instrumentation described herein (e.g., the inserter/impactors and distractors) will be discussed for use with the artificial intervertebral disc of FIGS. 1g-n of the '356 application (hereinafter, such figures will merely be referred to as "FIGS. 1g-n"), such discussions are merely by way of example and not intended to be limiting of their uses. Thus, it should be understood that the instrumentation and methods can be used with any of the artificial intervertebral discs disclosed in the '356 or '160 applications, or any other artificial intervertebral disc having (or being modifiable or modified to have) suitable features therefor. Moreover, it is anticipated that the features of the artificial intervertebral discs (e.g., plate surfaces, engagement holes, and baseplate teeth) that are used by the inserter/impactors and distractors discussed herein to hold and/or manipulate the artificial intervertebral disc can be applied, individually, or collectively or in various combinations, to other trials, spacers, artificial intervertebral discs, or other orthopedic devices as stand-alone innovative features for enabling such trials, spacers, artificial intervertebral discs, or other orthopedic devices to be more efficiently and more effectively held and/or manipulated by the inserter/impactors and/or distractors described herein or by tools having suitable features. In addition, it should be understood that the invention encompasses instrumentation and methods for implanting artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

Preferably, with regards to each artificial intervertebral disc to be implanted, a plurality of sizes of the artificial intervertebral disc would be available (e.g., the artificial intervertebral disc 160 of FIGS. 1g-n). That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. It should be understood that the artificial intervertebral discs can be offered in a variety of dimensions without departing from the scope of the invention, and that the dimensions specifically identified and quantified herein are merely exemplary. Each of the plurality of artificial intevertebral discs preferably further includes features that can be used by the inserter/impactors (described below) and/or the wedge-ramp and parallel insertion distractors (described below) and/or the inserter/impactor or other instruments described in the '356 application.

With regard to features that can be used by the inserter/impactors described here and in the '356 application, each artificial intervertebral disc includes an anteriorly facing flat surface, flanked by two anteriolaterally facing flat surfaces (one on each side of the anteriorly facing flat surface), and, to provide for holding of the disc for an anterior insertion approach, a hole spaced from the anteriorly facing flat surface, the hole having a longitudinal axis parallel to the anteriorly facing flat surface. The holding pin of the inserter/impactor fits within the hole, and the angled flat surfaces of the disc fit against the correspondingly angled flat surfaces of the inserter/impactor, and operation of the inserter/impactor pulls the holding pin toward the flat surface of the inserter/impactor opposite the pin, to rigidly hold the disc by the lower baseplate. The holding pin protrudes from the wedge-shaped extended surface of the distal end of the inserter/impactor and is restricted from upward movement with respect to the distal head by the presence of the wedge-shaped extended surface of the distal end of the inserter/impactor. More particularly, with any attempted upward movement of the holding pin, the pin encounters the upper surface of the channel in which the pin travels, preventing any such upward movement. When the intervertebral disc is held in this manner, rotation of the disc about a longitudinal axis relative to the inserter/impactor is prevented by interference of the corners of the disc's flat surfaces and the corners of the inserter/impactor's flat surfaces, similar to the manner in which a wrench holding a nut prevents rotation of the nut relative to the wrench. Further, when the disc is held in this manner, rotation of the disc about a lateral axis of the disc relative to the inserter/impactor is prevented by interference of the inwardly facing surface of the first baseplate (e.g., upper baseplate) of the disc and the corresponding surface (e.g., upper surface) of the wedge on the distal end, and by interference of the inwardly facing surface of the second baseplate (e.g., lower baseplate) of the disc and the corresponding surface (e.g., lower surface) of the wedge on the distal end. It is preferable that the wedge on the inserter/impactor will interfere between the first and second baseplates (e.g., upper and lower) so that the surfaces of the first and second baseplates align at a preferred 15 degrees angle of lordosis when the disc is held by the inserter/impactor.

Preferably, in order to provide for a holding of the disc for two additional (here, anteriolateral) insertion approaches, each disc also include two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the anteriolaterally facing flat surface (the one associated with the hole into which the pin is fit) of the disc against the flat surface of the inserter/impactor opposite the pin. It should be understood that preferably, in order to facilitate these two additional approaches, the angle separating the anteriorly facing flat surface of the disc and one of the anteriolaterally facing flat surfaces of the disc is equal to the angle separating the anteriorly facing flat surface and the other of the anteriolaterally facing flat surfaces.

With regard to features that can be used by the wedge-ramp distractor and the parallel insertion distractor of the present invention, each artificial intervertebral disc includes fixation teeth on the outwardly facing surface of the baseplate. Preferably, to permit them to ride in the grooves of the wedge-ramp distractor, two sets of teeth straddle the convex dome on the outwardly facing surface of each baseplate, and the teeth in each set are in straight rows.

BRIEF DESCRIPTION OF THE DRAWINGS

FIGS. 2a-c show side (FIG. 2a), perspective (FIG. 2b), and close-up perspective (FIG. 2c) views of a wedge plate inserter/impactor of the present invention.

DETAILED DESCRIPTION OF THE PREFERRED EMBODIMENTS

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of an artificial intervertebral disc (e.g., artificial intervertebral disc 160) for use with the instrumentation of the present invention is referenced and described in the '356 application, and the same description is hereby incorporated by reference herein. The artificial intervertebral disc illustrated in FIGS. 1g-n of the '356 application is discussed herein with reference to such figures, as an example of an artificial intervertebral disc suitable for use with the present invention.

A preferred embodiment of a wedge plate inserter/impactor of the present invention will now be described.

Figure 1G:
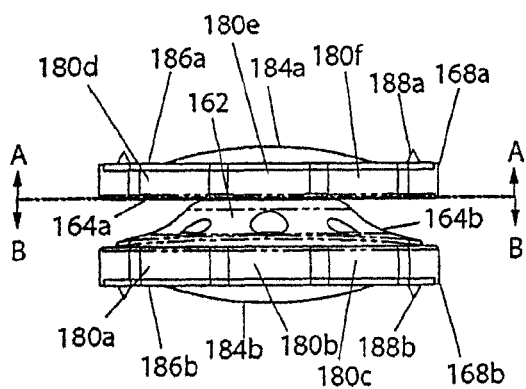
FIGS. 1g-n of the '356 application show front (FIG. 1g), side cutaway (FIG. 1h), top (FIG. 1i), perspective cutaway (FIG. 1j), bottom cutaway (FIG. 1k), top cutaway (FIG. 1l), bottom perspective (FIG. 1m), and top perspective (FIG. 1n) views of an exemplary artificial intervertebral disc for use with the present invention.
Figure 1H:
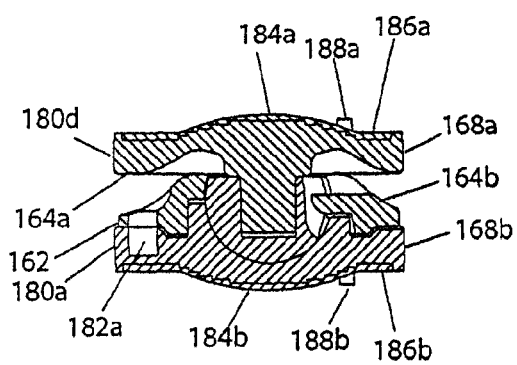
Figure 1I:
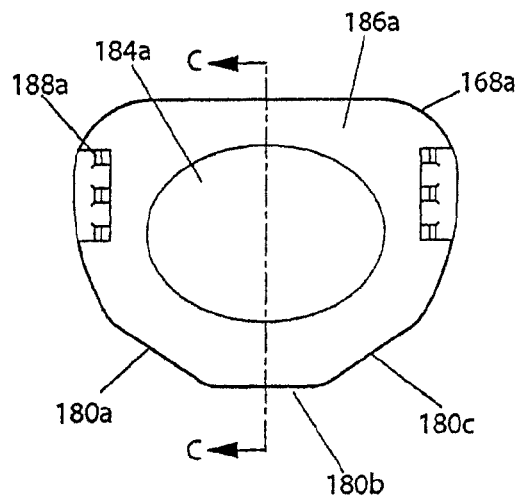
Figure 1J:
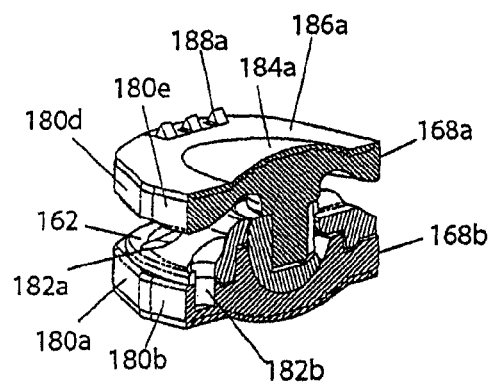
Figure 1K:
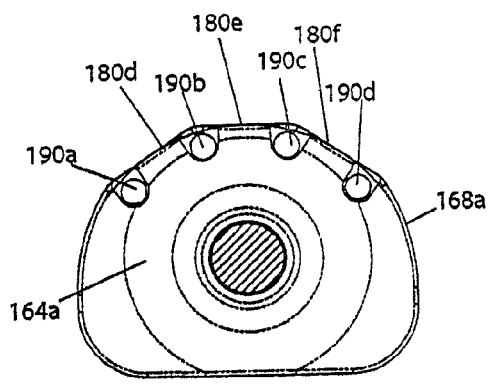
Figure 1L:
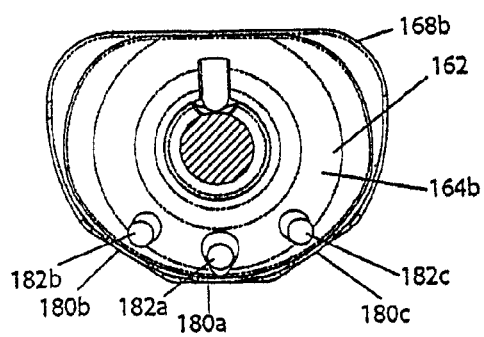
Figure 1M:
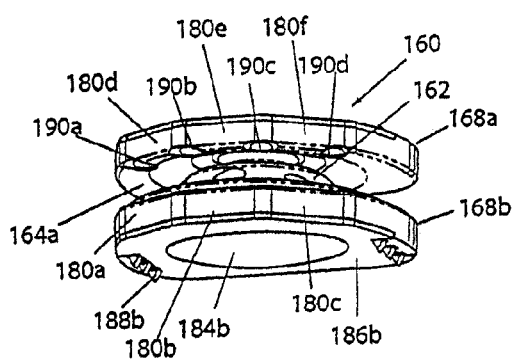
Figure 1N:
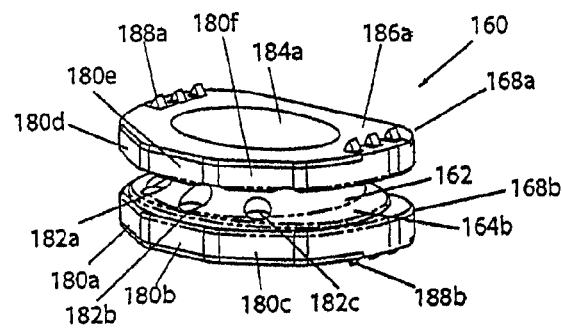
Figure 3A:
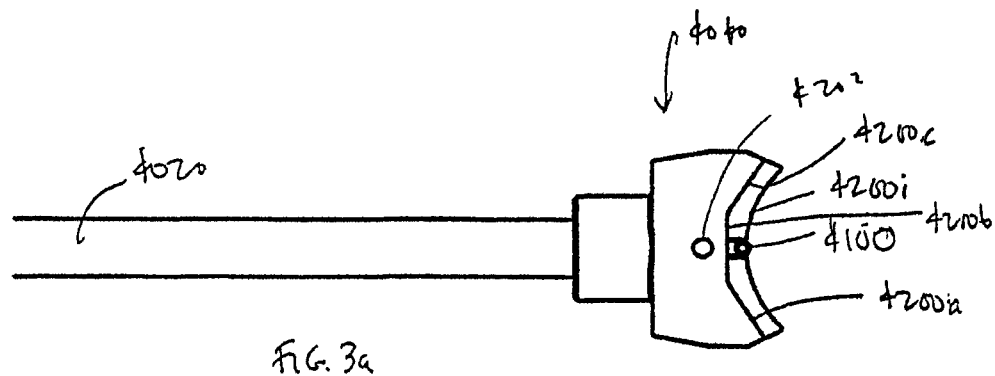
FIGS. 3a-d show bottom (FIG. 3a), side (FIG. 3b), top (FIG. 3c), and side cutaway (FIG. 3d) views of a distal end of a wedge plate inserter/impactor of the present invention.
Figure 3B:
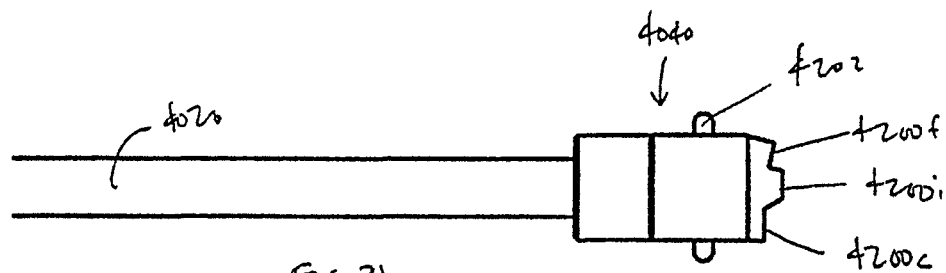
Figure 3C:
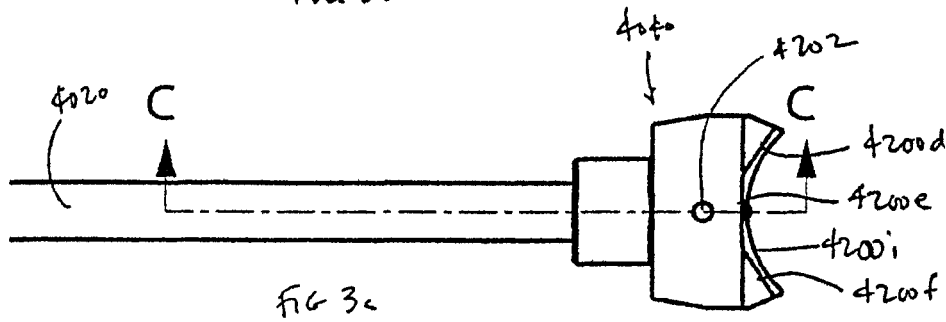
Figure 3D:
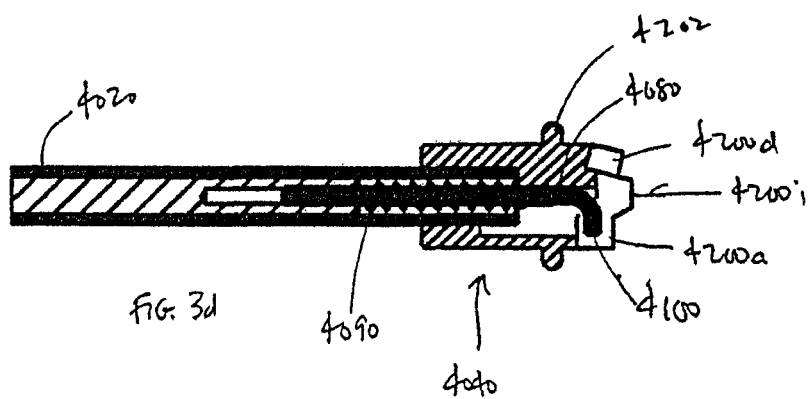
Figure 4A:
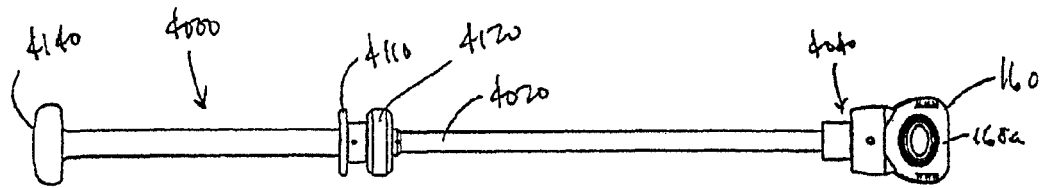
FIGS. 4a-b show top (FIG. 4a) and side (FIG. 4b) views of a wedge plate inserter/impactor of the present invention holding an exemplary artificial intervertebral disc.
Figure 4B:
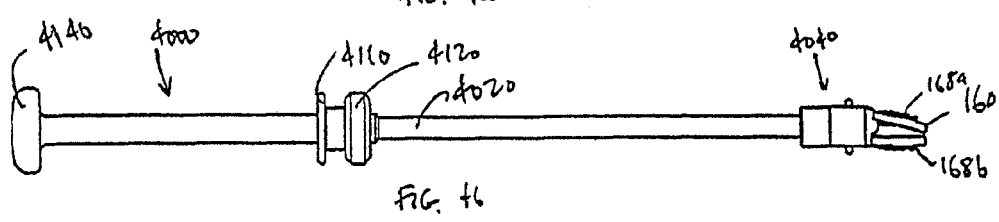
Figure 4C:
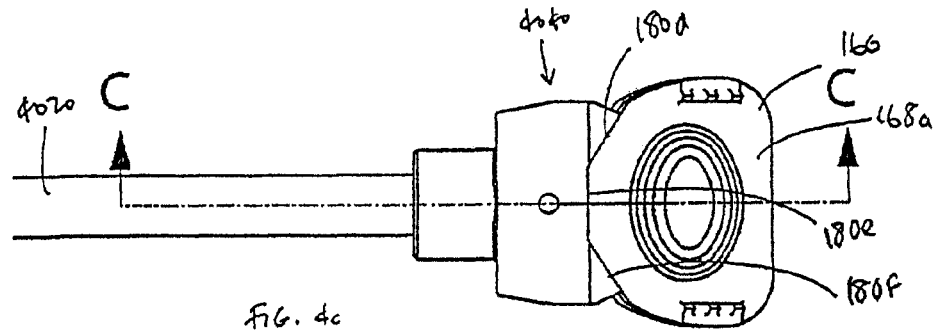
FIGS. 4c-e show top (FIG. 4c), side (FIG. 4d), and side cutaway (FIG. 4e) views of a distal end of a wedge plate inserter/impactor of the present invention holding an exemplary artificial intervertebral disc.
Figure 4D:
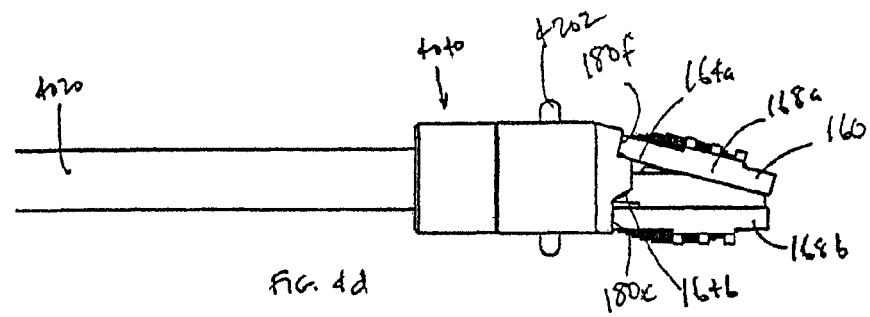
Figure 4E:
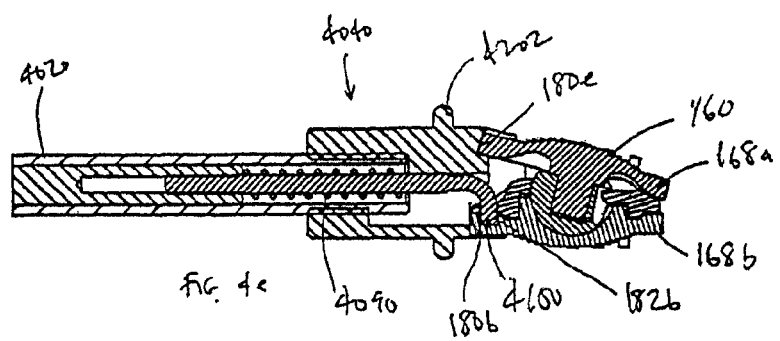

Referring now to FIGS. 2a-4e, FIGS. 2a-c side (FIG. 2a), perspective (FIG. 2b), and close-up perspective (FIG. 2c), and perspective (FIG. 4d) views of a wedge plate inserter/impactor of the present invention. FIGS. 3a-d show bottom (FIG. 3a), side (FIG. 3b), top (FIG. 3c), and side cutaway (FIG. 3d) views of a distal end of a wedge plate inserter/impactor of the present invention. FIGS. 4a-b show top (FIG. 4a) and side (FIG. 4b) views of a wedge plate inserter/impactor of the present invention holding an exemplary artificial intervertebral disc. FIGS. 4c-e show top (FIG. 4c), side (FIG. 4d), and side cutaway (FIG. 4e) views of a distal end of a wedge plate inserter/impactor of the present invention holding an exemplary artificial intervertebral disc.

It should be understood that the illustration and reference herein to the artificial intervertebral disc shown in FIGS. 1g-n of the '356 application is merely to show an example of one type of artificial intervertebral disc that is contemplated by, encompassed by, and suitable for use with, the present invention, and that such illustration and reference herein is not meant to limit the scope of the present invention or limit the uses of the present invention. Rather, any other artificial intervertebral disc (or any other orthopedic device) having suitable features for being used with the instrumentation and methods described herein are contemplated by the present invention. Indeed, the features suitable for manipulation (e.g., angled flat surfaces with adjacent holes and/or opposing notches, and/or inwardly facing baseplate surfaces) are encompassed by the present invention, regardless of to what orthopedic device they may be applied. Other exemplary suitable artificial intervertebral discs include, but are not limited to, the artificial intervertebral discs described in the '160 application with regard to FIGS. 8a-y, 9a-t, 10a-t, 11a-j, and 12a-o thereof and by the accompanying descriptions therefor (e.g., embodiments identified as the first, second, third, fourth, and fifth preferred embodiments of the fourth embodiment family, etc.). It should be noted that, as can be seen from FIGS. 1g-n of the '356 application, that the artificial intervertebral disc shown in FIGS. 1g-n of the '356 application has features similar to those of these other suitable artificial intervertebral discs of the '160 application, and it should be understood that such similar features are structurally and functionally as described in the '160 application. Such similar features include an inwardly facing surface of the upper baseplate, and a convex structure on the lower baseplate, the convex structure having an inwardly facing surface.

And, while the instrumentation described herein (e.g., the inserter/impactor) as well as the instrumentation described in the '356 application (e.g., the inserter/impactor described therein) will be discussed for use with the artificial intervertebral disc of FIGS. 1g-n of the '356 application, such discussions are merely by way of example and not intended to be limiting of their uses. Thus, it should be understood that the tools can be used with any of the artificial intervertebral discs disclosed in the '356 application or the '160 application, or any other artificial intervertebral disc having (or being modifiable or modified to have) suitable features therefor. Moreover, it is anticipated that the features of the artificial intervertebral disc (e.g., the angled flat surfaces and the inwardly facing baseplate surfaces, and accompanying holes) that are used by the tool discussed herein (or in the '356 application) to hold and/or manipulate these devices (certain features, it should be noted, were first shown and disclosed in the '160 application, the '127 application, and/or the '356 application) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein (or in the '356 application) or by other tools having suitable features. In addition, it should be understood that the invention encompasses artificial intervertebral discs, spacers, trials (static or dynamic), and/or other orthopedic devices, that have one or more of the features disclosed herein (or in the '356 application), in any combination, and that the invention is therefore not limited to artificial intervertebral discs, spacers, trials, and/or other orthopedic devices having all of the features simultaneously.

Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs.

The inserter/impactor 4000 is provided primarily for holding, inserting, repositioning, removing, impacting, extracting, and otherwise manipulating an artificial intervertebral disc having features suitable for being manipulated by the inserter/impactor. (However, it can also be used to hold, insert, reposition, remove, impact, extract, and otherwise manipulate any other orthopedic device having suitable features therefor. For example, it should be understood that distraction of an intervertebral space can be accomplished in conjunction with a cooperating tool or spacer that can be gripped by the inserter/impactor.) Exemplary suitable artificial intervertebral discs include, but are not limited to, the artificial intervertebral disc 160 described herein and the artificial intervertebral discs described in the '160 application with regard to FIGS. 8*a-y*, 9*a-t*, 10*a-t*, 11*a-j*, and 12*a-o* thereof and by the accompanying descriptions therefor (e.g., embodiments identified as the first, second, third, fourth, and fifth preferred embodiments of the fourth embodiment family, etc.). Regarding the features suitable for being manipulated by the inserter/impactor 4000, such features include those discussed above as being suitable features on the disc 160, namely, an anteriorly facing flat surface on the second (e.g., lower) baseplate of the trial or disc, flanked by two anteriolaterally facing flat surfaces (one on each side of the anteriorly facing flat surface), and, to provide for holding of the trial or disc for an anterior insertion approach, a hole spaced from the anteriorly facing flat surface, the hole having a longitudinal axis parallel to the anteriorly facing flat surface. Further regarding the features suitable for being manipulated by the inserter/impactor, such features further include the inwardly facing surfaces of the baseplates of the disc.

More particularly, the inserter/impactor 4000 includes a shaft 4020 having a distal end 4040 that has angled flat surfaces 4200*a-c* corresponding to and fittable against angled flat surfaces of the artificial intervertebral disc (e.g., the surfaces 180*a-c* of the artificial intervertebral disc 160) to be implanted. The distal end 4040 has angled flat surfaces 4200*d-f* corresponding to and fittable against angled flat surfaces of the artificial intervertebral disc (e.g., the surfaces 180*d-f* of the artificial intervertebral disc 160) to be implanted. The distal end 4040 has a wedge-shaped extension 4042 including upper 4200*g* and lower 4200*h* wedge surfaces corresponding to and fittable against the inwardly facing surfaces of the artificial intervertebral disc (e.g., the lower surface 164*a* of the upper baseplate 168*a* of the disc 160, and the upper surface 164*b* of the lower baseplate 168*b* of the disc 160, respectively) to be implanted. For example, in an anterior approach for the disc 160 (as shown in FIGS. 4*a-e*), 180*a* and 180*d* facing 4200*a* and 4200*d*, 180*b* and 180*e* facing 4200*b* and 4200*e*, 180*c* and 180*f* facing 4200*c* and 4200*f*, and 164*a* facing 4200*g* and 164*b* facing 4200*h*.

The inserter/impactor 4000 holds the disc 160 in a preferred position with respect to the inserter/impactor 4000. (It should be understood that the surfaces of the wedge-shaped extension 4042 can be modified within the scope of the present invention to hold the disc 160 (or another orthopedic device) at positions other than those illustrated herein.) In the illustrated embodiment of the inserter/impactor 4000 in use with the disc 160, the preferred position is with the baseplates 168*a,b* of the disc 160 angled at 15 degrees of lordosis with respect to one another. More particularly, preferably, the upper and lower surfaces (e.g., 4200*g* and 4200*h*) of the wedge-shaped extension 4042 protrude from the distal end 4040 and are formed to hold the baseplates 168*a,b* such that they are angled at 15 degrees of lordosis with respect to one another. A surface (e.g., lower surface 4200*h*) of the wedge-shape extension 4042 that mates with an inwardly facing surface of a baseplate (e.g., the lower baseplate 168*b*) of a disc (e.g., 160) may be correspondingly shaped (e.g., curved or flat) for interaction or mating with the disc baseplate (e.g., the lower surface 4200*h* of the wedge-shaped extension as illustrated is curved to accommodate the surface of the shield of the disc). Preferably, the forward surface 4200*i* of the wedge-shaped extension 4042 has a concave curvature towards the shaft 4020 of the inserter/impactor 4000, also for accommodating the curvature of the surface of the shield of the disc.

Also preferably with regard to the preferred positioning, the wedge surfaces of the distal end 4040 protrude from a distance midway with respect to the top and bottom of the distal end 4040 and span (e.g., right to left or vice-versa) the entire distal face of the distal end 4040, and the surfaces 4200*d-f* above the wedge on the distal end 4040 are respectively perpendicular to the wedge's upper surface 4200*g* such that each is disposed in parallel with its respective corresponding surface of the disc 160 when the disc 160 is held by the inserter/impactor 4000 at the appropriate lordosis angle. (And, accordingly, are angled approximately 15 degrees with respect to the surfaces below the wedge 4200*a-c*.) Preferably, for an anterior approach, the wedge-shaped extension 4042 is designed and shaped to fit with its antero-lateral confronting surfaces (4200*d,f* and 4200*a,c*) tightly against the correspondingly antero-laterally facing surfaces (180*d,f* and 180*a,c*) of the disc 160, but such that its anterior confronting surfaces (4200*e* and 4200*b*) are slightly spaced from the anteriorly facing surfaces (180*d* and 180*b*) of the disc 160, when the disc is held by the inserter/impactor 4000. This is primarily to address manufacturing issues (in some cases, tolerances may not be adequately defined to ensure that all of those surfaces fit tightly against their corresponding surfaces), so that if there are manufacturing anomalies, any slight tolerance differences that may exist are nevertheless still adequate to ensure at least the tight fitting of the antero-lateral confronting surfaces, so that manipulation of the disc 160 is possible (e.g., in the manner of a wrench against an angled nut). This can be achieved, e.g., by designing the anterior confronting surfaces (4200*e* and 4200*b*) to each be slightly greater in length than the corresponding anteriorly facing surfaces (180*e* and 180*b*) of the disc baseplates, while still being angled with respect to the antero-lateral confronting surfaces (4200*d,f* and 4200*a,c*) at the same angle the antero-laterally facing surfaces (180*d,f* and 180*a,c*) of the disc baseplates are angled with respect to the anteriorly facing surfaces (180*e* and 180*b*) of the disc. The increased length of the anterior confronting surfaces on the wedge extension results in the slight clearance between the anteriorly facing surfaces (180*e* and 180*b*) of the disc and the corresponding anterior confronting surface (4200*e* and 4200*b*) of the wedges and distal end, thereby ensuring that the disc will be fully seated against the antero-lateral confronting surfaces of the distal end despite possible manufacturing, material or other inevitable variations in tolerances of the artificial intervertebral disc or the inserter/impactor. As noted above, similar in this regard to the manner in which a wrench engages a nut, this fitting increases the mechanical advantage toward repositioning the disc in the intervertebral space. It should be noted, inasmuch as the inserter/impactor 4000 described herein can engage the disc from the antero-lateral angles as well, the anterior confronting surfaces (4200*e* and 4200*b*) should also be longer than the antero-laterally facing surfaces (180*d,f* and 180*a,c*) of the disc, so that a similar fitting occurs when the disc is held from the antero-lateral angles. Stated broadly, the primary confronting surfaces (e.g., the anterior confronting surfaces) of the inserter/impactor are preferably slightly longer than the primary confronted surfaces (e.g., anteriorly facing surfaces) of the disc for any given holding orientation.

Further, the inserter/impactor 4000 includes a holding pin 4080 that extends from the wedge 4042 along a longitudinal axis of the shaft 4020, the pin 4080 having a distal end 4100 that is bent downwardly. The holding pin 4080 is spring loaded (e.g., by a spring 4090) in a central channel of the shaft 4020, so that it is biased toward the shaft 4020 (preferably, the bent end 4100 of the pin 4080 prevents it from entering the central channel). The holding pin 4080 is restricted from upwardly lateral movement with respect to the distal end of the inserter/impactor by the presence of the wedge-shaped extension 4042 of the distal end 4040 of the inserter/impactor 4000. More particularly, with any attempted upward movement of the holding pin 4080, the pin encounters the upper surface of the channel in which the pin 4080 travels, preventing any such upward movement. The holding pin 4080 is preferably heat treated (e.g., cold formed) to increase material quality (e.g., strength).

A flange 4110, mechanically connected to the pin 4080 and translating adjacent the shaft 4020, can be pushed distally to overcome the bias of the spring 4090 to space the pin 4080 away from the wedge 4042. (An alternative configuration is one in which the flange 4110 and the pin 4080 are formed from a single piece, rather than being mechanically connected.) In this extended position, the pin 4080 can be inserted in a hole (e.g., 182*b*) in the baseplate (e.g., 168*b*) of the artificial intervertebral disc (e.g., 160). Releasing the flange 4110 allows the spring 4090 to pull the pin 4080 back, causing the anteriorly facing surface 180*b* of the baseplate 168*b* to be held against the lower central flat surface 4200*b* of the inserter/impactor 4000 and the anterioloaterally facing flat surfaces 180*a,c* of the artificial intervertebral disc 160 to be held against the other corresponding flat surfaces 4200*a,c* of the inserter/impactor 4000. This can be further understood in light of the description of the manner in which the inserter/impactor of the '160 application functions to grip an orthopedic device, which is included in the '160 application and incorporated by reference herein. Simultaneously, the anteriorly facing surface 180*e* of the baseplate 168*a* is pulled against the upper central flat surface 4200*e* of the inserter/impactor 4000 and the anterioloaterally facing flat surfaces 180*d,f* of the artificial intervertebral disc 160 is pulled against the other corresponding flat surfaces 4200*d,f* of the inserter/impactor 4000. Additionally, the upper and lower wedge surfaces (4200*g,h*) interfere between the inwardly facing surfaces 164*a,b* of the disc baseplates, causing the baseplate to be angled at a 15 degree lordosis angle, with the lower surface 164*a* of the upper baseplate 168*a* held against the upper surface 42008, and the upper surface of the shield being held against the lower surface 4200*h*, as best shown in FIGS. 4*a-e*.

A knob 4120, threaded on the shaft 4020, can be rotated about the longitudinal axis of the shaft 4020 to push the flange 4110 farther proximally, to pull the pin 4090 tighter and therefore lock its position (the interference of the threads of the knob-shaft interface prevents the knob 4120 from moving distally unless the knob 4120 is reverse rotated to effect that result) to more securely hold the baseplate 168*b*, and reverse rotated to unlock and loosen the pin 4080.

When the disc 160 is held in this manner, rotation of the disc 160 about a longitudinal axis (of the disc 160) relative to the inserter/impactor 4000 is prevented by interference of the corners of the disc's 160 flat surfaces (180*a-c* and 180*d-f*) and the corners of the inserter/impactor's 4000 flat surfaces (4200*a-c* and 4200*d-f*), similar to the manner in which a wrench holding a nut prevents rotation of the nut relative to the wrench. Further, the holding of the disc 160 in this manner allows for some repositioning of the disc 160 in the intervertebral space via rotation of the disc 160 in either direction about the longitudinal axis of the intervertebral space. Further when the disc is held in this manner, rotation of the disc about a lateral axis (of the disc 160) relative to the inserter/impactor 4000 is prevented by interference of the inwardly facing surface 164*a* of the first baseplate (e.g., upper baseplate) of the disc and the upper surface 4200*g* of the wedge on the distal end 4040, and by interference of the inwardly facing surface 164*b* of the second baseplate (e.g., lower baseplate) of the disc and the lower surface 4200*h* of the wedge on the distal end 4040. Accordingly, the holding of the disc in this manner allows for some repositioning of the disc in the intervertebral space via rotation of the disc in either direction about the longitudinal or latitudinal axis of the intervertebral space In some embodiments, when the artificial intervertebral disc 160 is held by the inserter/impactor 4000, the flat surfaces 180*a-c* are more closely confronted by the angled flat surfaces 4200*a-c* of the inserter/impactor 4000, compared with the flat surfaces 180*d-f* being less closely confronted by the angled flat surfaces 4200*d-f* of the inserter/impactor 4000. As such, the structure of the artificial intervertebral disc 160 having the flat surfaces 180*d-f* (e.g., the upper baseplate 168*a*) has slightly more rotation and angulation freedom relative to the inserter/impactor 4000 when being held, compared to the structure of the artificial intervertebral disc 160 having the flat surfaces 180*a-c* (e.g., the lower baseplate 168*b*). This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted.

Preferably, in order to provide for a holding of the disc 160 for two additional (here, anterolateral) insertion approaches, each disc 160 also includes two additional holes 182a and 182c, one (e.g., 182a) spaced apart from one of the anteriolaterally facing flat surfaces (e.g. 180a), and the other (e.g. 182c) spaced apart from the other of the anteriolaterally facing flat surfaces (e.g. 180c). Accordingly, operation of the inserter/impactor 4000 can fit the holding pin 4080 into either of these two additional holes 182a or 182c, and hold the associated anteriolaterally facing flat surface (the one associated with the hole into which the pin 4080 is fit) of the disc 160 against the flat surface of the inserter/impactor 4000 opposite the pin 4080. For example, in a first anterolateral approach for the disc 160, 180a and 180d facing 4200b and 4200e, 180c and 180f not confronted, and 180b and 180e facing 4200c and 4200f, and in a second anterolateral approach for the disc 160, 180b and 180e facing 4200a and 4200d, 180a and 180d not confronted, and 180c and 180f facing 4200b and 4200e. It should be understood that preferably, in order to facilitate these additional approaches, the angle separating the anteriorly facing flat surface of the disc 160 and one of the anteriolaterally facing flat surfaces of the disc 160 is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces (or placing the angulated surfaces in other locations on the disc or other orthopedic device), and/or including corresponding holes adjacent to such surfaces, can provide the surgeon with additional approaches, e.g., other anterolateral approaches, directly lateral approaches, posteriolateral approaches, and/or directly posterior approaches. For example, a trial or disc can have angled surfaces (and corresponding holes) along the entire perimeter of one or both of the baseplates, and thus enable the surgeon to engage the trial or disc from a number of angles, including anterior, posterior, lateral, anterolateral, and posteriolateral angles.

The inserter/impactor 4000 further includes at a proximal end a cap 4140 for use as an impact surface if the disc 160 must be impacted further into the intervertebral space after insertion, or forcibly extracted from the intervertebral space. A mallet can be used to strike the cap 4140 (in a distal direction for impaction, or in a proximal direction (using the flange of the cap 4140) for extraction). It should be noted a striking of the cap 4140 will translate the striking force to the baseplates through the shaft 4020 and the flat surfaces, but will not damage the holding pin 4080 because the holding pin 4080 is spring loaded in the central channel and thus buffered from the striking force thereby. The distal end 4040 of the inserter/impactor 4000 further preferably includes at least one vertebral body stop 4202 that protrudes longitudinally with respect to the shaft 4020, from the surfaces of the distal end. The stops help prevent the inserter/impactor from being used to insert the disc (or other orthopedic device) too far into the intervertebral space.

Accordingly, the inserter/impactor 4000 can be used to grip the artificial intervertebral disc to be implanted, and hold the same during insertion and/or removal of the same, and is useful for a variety of surgical approach angles.

Figure 5:
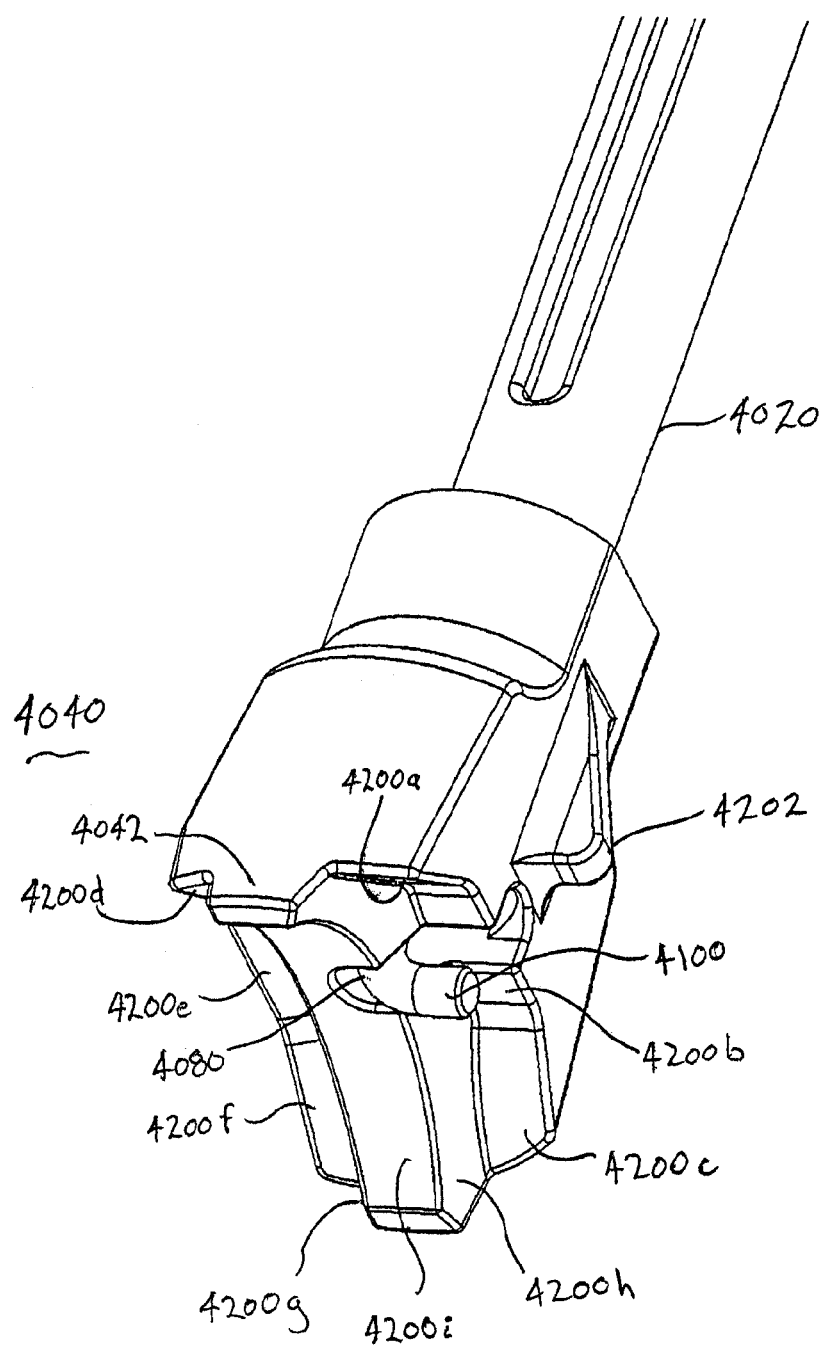
FIG. 5 shows a close-up perspective view of a preferred embodiment of the distal end of a wedge plate inserter/impactor of the present invention.
Figure 6:
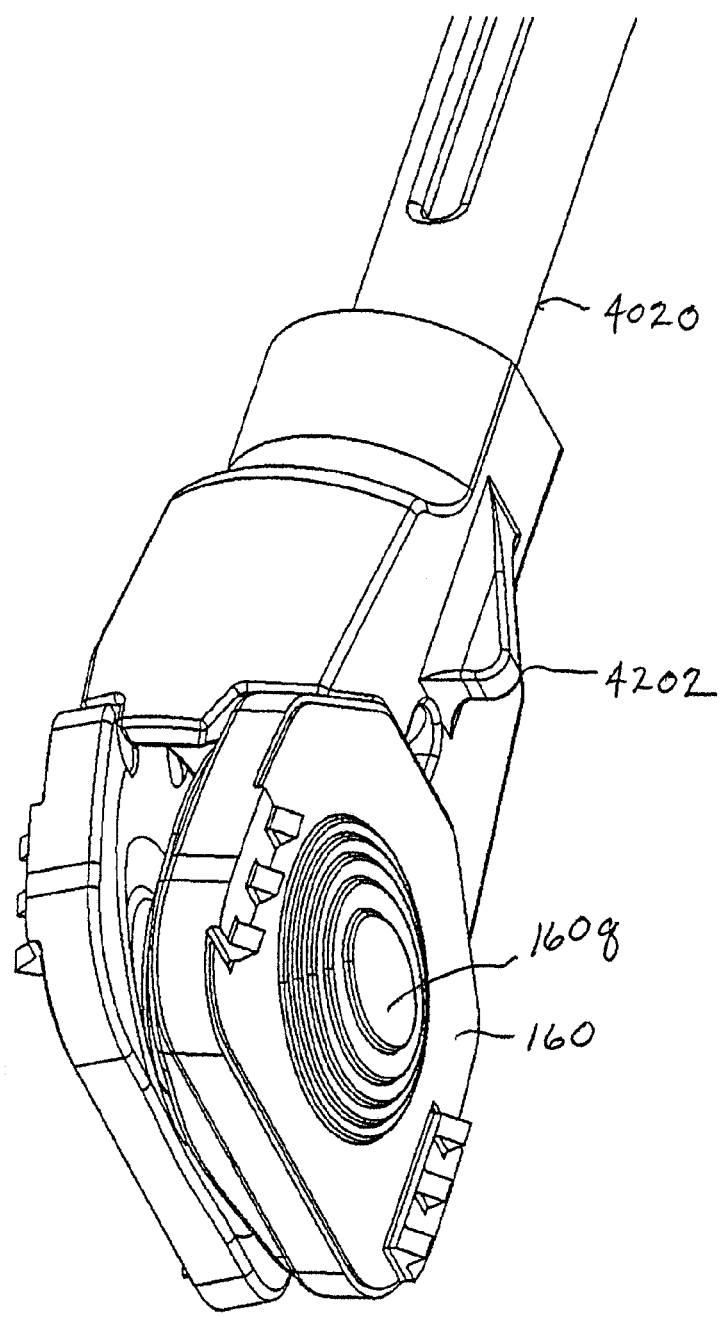
FIG. 6 shows a close-up perspective view of the distal end of a wedge plate inserter/impactor of the present invention according to FIG. 5 holding an exemplary artificial intervertebral disc.

Now referring to FIGS. 5 and 6, a preferred embodiment of inserter/impactor 4000 is described. In this embodiment at least one vertebral body stop 4202 has a ramped configuration, the ramp tapering from its peak adjacent the distal face of distal end 4040 toward the proximal end of inserter/impactor 4000. This configuration of the stop 4202 assists in preventing the inserter/impactor 4000 from overinserting the disc (or other orthopedic device) into the intervertebral space and also permits the inserter/impactor to 4000 to be employed in conjunction with the distractor shown in FIGS. 7-9, as described below.

As best seen in FIG. 6, in a preferred embodiment inserter/impactor 4000 is sized such that its thickness, excluding stop(s) 4202, is less than that of disc 160 so that the disk 160 has the largest profile of any part introduced in the intervertebral space. Diminishing the profile of the inserter/impactor 4000 has the benefit of minimizing the possibility of unintentional injury to the intervertebral space, as well as permitting the inserter/impactor 4000 to be inserted between the wedge-ramps (described below) while holding the disc 160.

Figure 7:
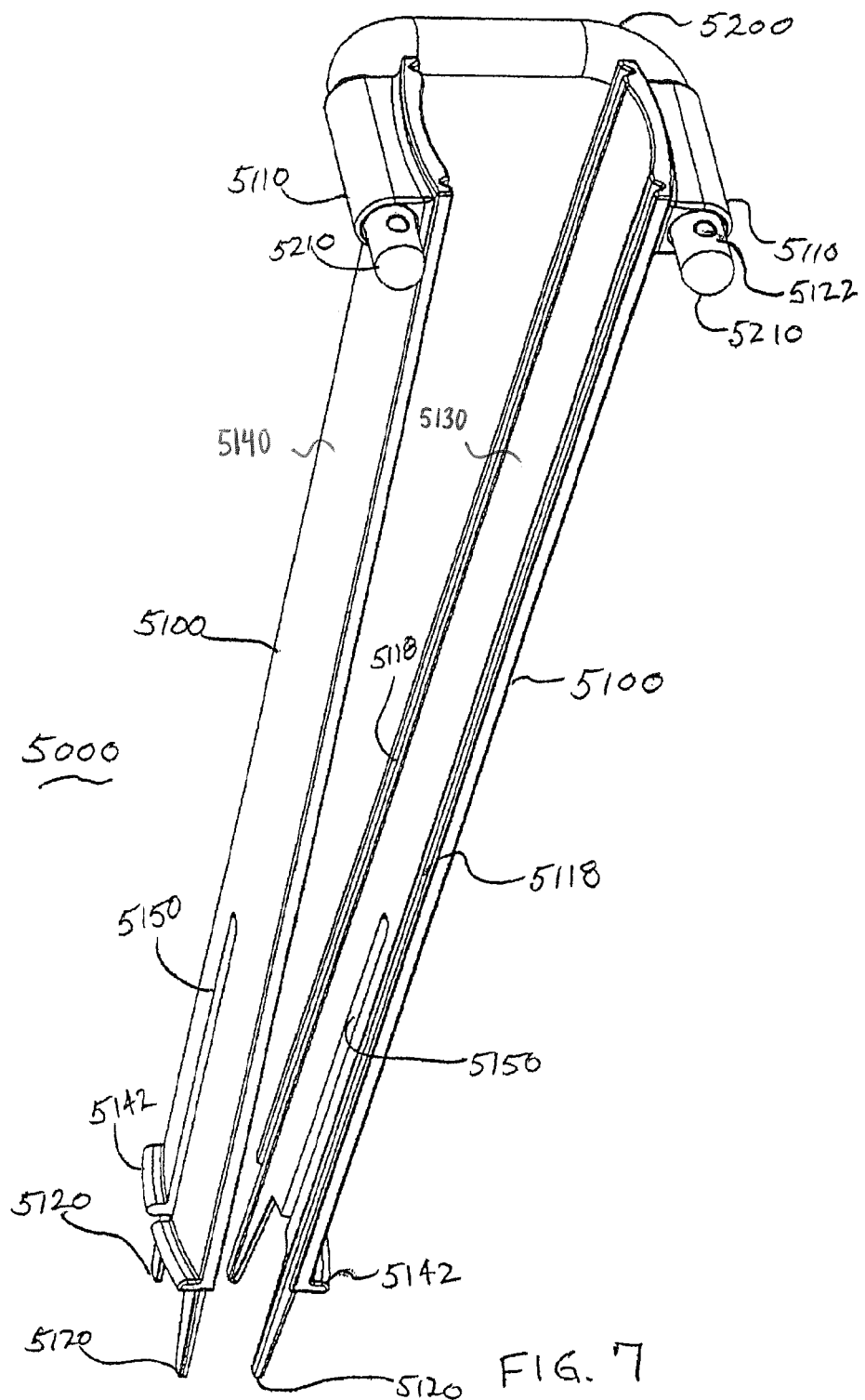
FIG. 7 shows a perspective view of a wedge ramp distractor of the present invention.
Figure 8:
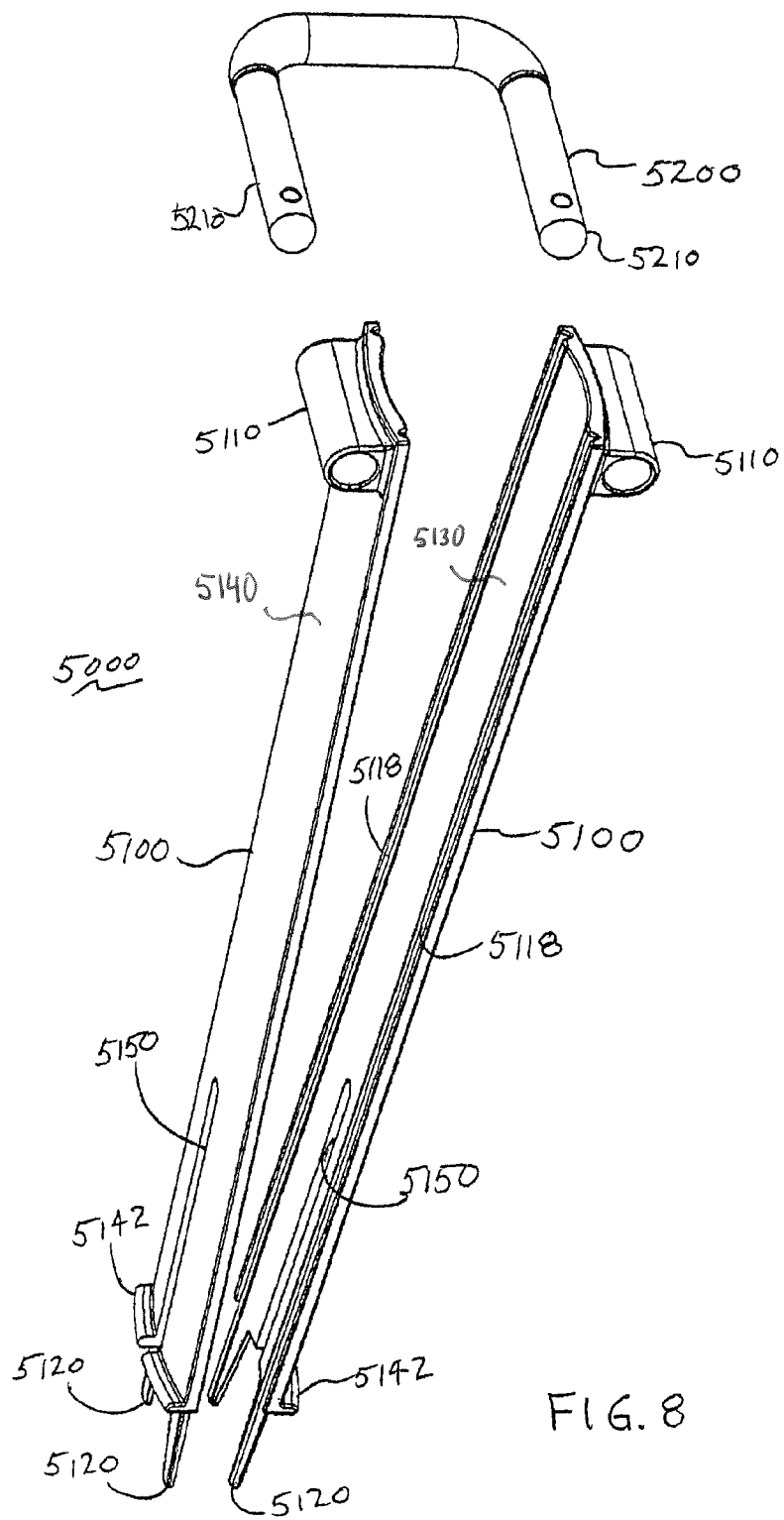
FIG. 8 shows a perspective view of the wedge ramp distractor of the present invention according to FIG. 7 in disassembled form.
Figure 9:
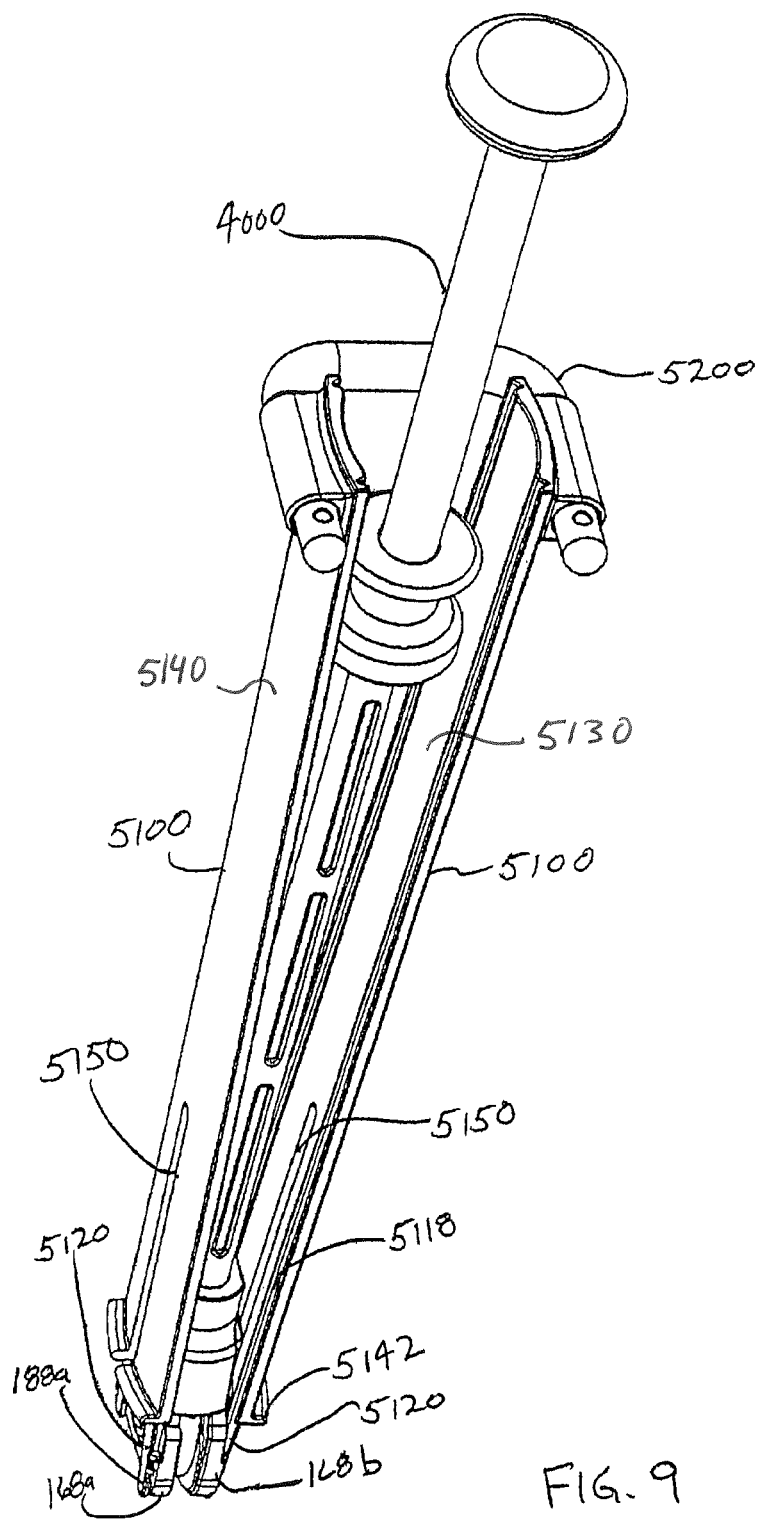
FIG. 9 shows a perspective view of the wedge ramp distractor of the present invention according to FIG. 7 having inserted therein the wedge plate inserter/impactor of the present invention according to FIG. 5 holding an exemplary artificial intervertebral disc.

Now referring to FIGS. 7-9 a preferred embodiment of a distractor is disclosed. A distractor 5000 comprises essentially a pair of identical ramps 5100 facing one another and converging toward one another, and a connecting member (e.g., c-clip) 5200 having extensions (e.g., legs) 5210 for operably connecting ramps 5100 to each other. The use of multiple pieces eases cleaning of the distractor 5000 in an autoclave, and the use of the c-clip 5200 allows the ramps 5100 to be doubly-hinged to one another for ease of extraction of the ramps 5100 from the intervertebral space. In an alternate embodiment distractor 5000 is formed as a unitary device. The distractor 5000 is sized to correspond to the baseplate footprint of the disc 160 that is to be implanted, such that, preferably, the teeth 188a, 188b (or other suitable engagement features) of the disc 160 are able to travel in a corresponding guide feature (e.g., grooves 5118) in the ramps 5100 (as described below).

Ramp 5100 has a connecting member receipt feature (e.g., channel) 5110 disposed on its proximal end for receiving a leg 5210 of c-clip 5200. The interior side 5130 of ramp 5100, i.e., the side that faces opposing ramp 5100, is defined by guide features (e.g., laterally spaced grooves) 5118 disposed longitudinally on the interior side 5130 and extending along intervertebral space engagement members (e.g., laterally spaced prongs) 5120 extending from the distal end of ramp 5100. The exterior side 5140 of ramp 5100 is defined by vertebral body stop features (e.g., transversely disposed ridges) 5142 formed at the base of prongs 5120 adjacent the distal end of ramp 5100. An instrument accommodation feature (e.g., longitudinal aperture 5150) is formed medially in ramp 5100 and, e.g., extends from the distal end of said ramp 5100 substantially parallel to grooves 5118 partially along the length of ramp 5100.

C-clip 5200 further comprises a fastening device for securely but removably engaging channel 5110, such as, but not limited to, a floating ball bearing 5122 that permits a leg 5120 of the c-clip to slidably and lockably engage channel 5110.

Now further referring to FIG. 9, as assembled, grooves 5118 of the respective ramps 5100 face one another. In this orientation, inserter/impactor 4000 (having the disc 160 mounted thereto) is insertable between the opposing ramps 5100, with the teeth 188a of the implant base plates 168a-b slidably engaging grooves 5118.

In practice, prongs 5120 are inserted between the vertebral endplates at the lion site. Ridges 5142 prevent overinsertion of the prongs 5120 into the Intervertebral space as the ridges 5142 confront the anterior faces of the vertebral bodies. Once the prongs 5120 are inserted, the disc 160, already secured to the inserter/impactor 4000, is placed onto the bottom ramp 5100 such that the teeth 188a "ride" in the grooves 5118 as the disc 160 is pushed forward along the length of the bottom ramp 5100. The disc 160 is preferably oriented such that the bottom base plate 168b is parallel to the ramp 5100 and the top base plate 168a is held in a lordosed position relative to the bottom base plate 168b by the inserter/impactor 4000. Also, aperture 5150 accommodates the vertebral body stops 4202 (having the ramped configuration) of a preferred embodiment of inserter/impactor 4000 (as shown in FIGS. 5-6) during the forward movement of the disc 160 and inserter/impactor 4000. (This configuration of the stop 4202 not only assists in preventing the inserter/impactor 4000 from overinserting the disc 160 (or other orthopedic device) into the intervertebral space (by the confrontation of the distal end of the stops 4202 with the anterior faces of the vertebral endplates), but also permits the inserter/impactor to 4000 to be easily withdrawn if it is necessary to remove or extract the disc 160 prior to removing the ramps 5100 from the treatment site (as the inserter/impactor 4000 is pulled backwards between the ramps 5100, the taper of the ramped proximal portion of the stop 4202 enables the stop to not catch on the proximal end of aperture 5150, but rather to smoothly transition from the proximal end of aperture 5150 to the remaining proximal portion of the ramp 5100.)

Continued movement of the disc 160 toward the intervertebral space is typically met with increased resistance as the space is distracted (by the wedging action of the disc 160 being pushed forward and thereby separating the prongs 5120) to accommodate the height of the disc 160; manual pressure typically overcomes this resistance. If necessary, a proximal flange 4140 on the inserter/impactor 4000 can be struck to effect any additional force required. With regard to the configuration of the prongs 5120, the prongs 5120 are preferably dimensioned to facilitate guidance and passage of the disc 160 into the intervertebral space after leaving the distal portion of the ramps 5100 past the ridges 5142, and out from the intervertebral space once the disc 160 is disposed therein. More particularly, the prongs 5120 are dimensioned in width to slidably fit between the convex dome 184a, 184b and the teeth 188a, 188b on the disc 160 baseplates, and dimensioned in length to reach far enough into the intervertebral space to provide leverage support for the wedging action. Once the disc 160 is inserted into the intervertebral space, the ramps 5100 are removed from the intervertebral space, preferably one at a time by first rotating the top ramp 5100 out from between the disc 160 and the upper vertebral endplate using the c-clip 5200 as a double-hinge. The bottom ramp 5100 may then be pulled out from between the disc 160 and the lower vertebral endplate. The inserter/impactor 4000 may then be removed from the disc 160. Further with regard to the configuration of the prongs 5120, the prongs' 5120 dimensions preferably facilitate removal of the prongs 5120 as the ramps 5100 are pulled out (i.e., the pulling out of the ramps 5100 slides the prongs 5120 between the convex dome 184a, 184b and the teeth 188a, 188b of the disc 160, to avoid damage to the disc 160 or the vertebral endplate.

It should be noted that the use of the prongs 5120 and the grooves 5118 thereon, in which the teeth 188a, 188b slide, avoids any possible damage to the vertebral endplates as a result of engagement of the endplate by the teeth 188a, 188b prior to full insertion of the disc 160. That is, using the above-described method, the teeth 188a, 188b do not engage the endplate until after the prongs 5120 are removed, which is once the disc 160 is properly placed, and therefore the initial engagement of the endplate by the teeth 188a, 188b is the final engagement. Accordingly, because no gouging or scratching of the endplate by the teeth 188a, 188b occurs, the teeth 188a, 188b are less likely to move from their engaged position, which provides a more secure foothold for the disc 160.

Figure 10:
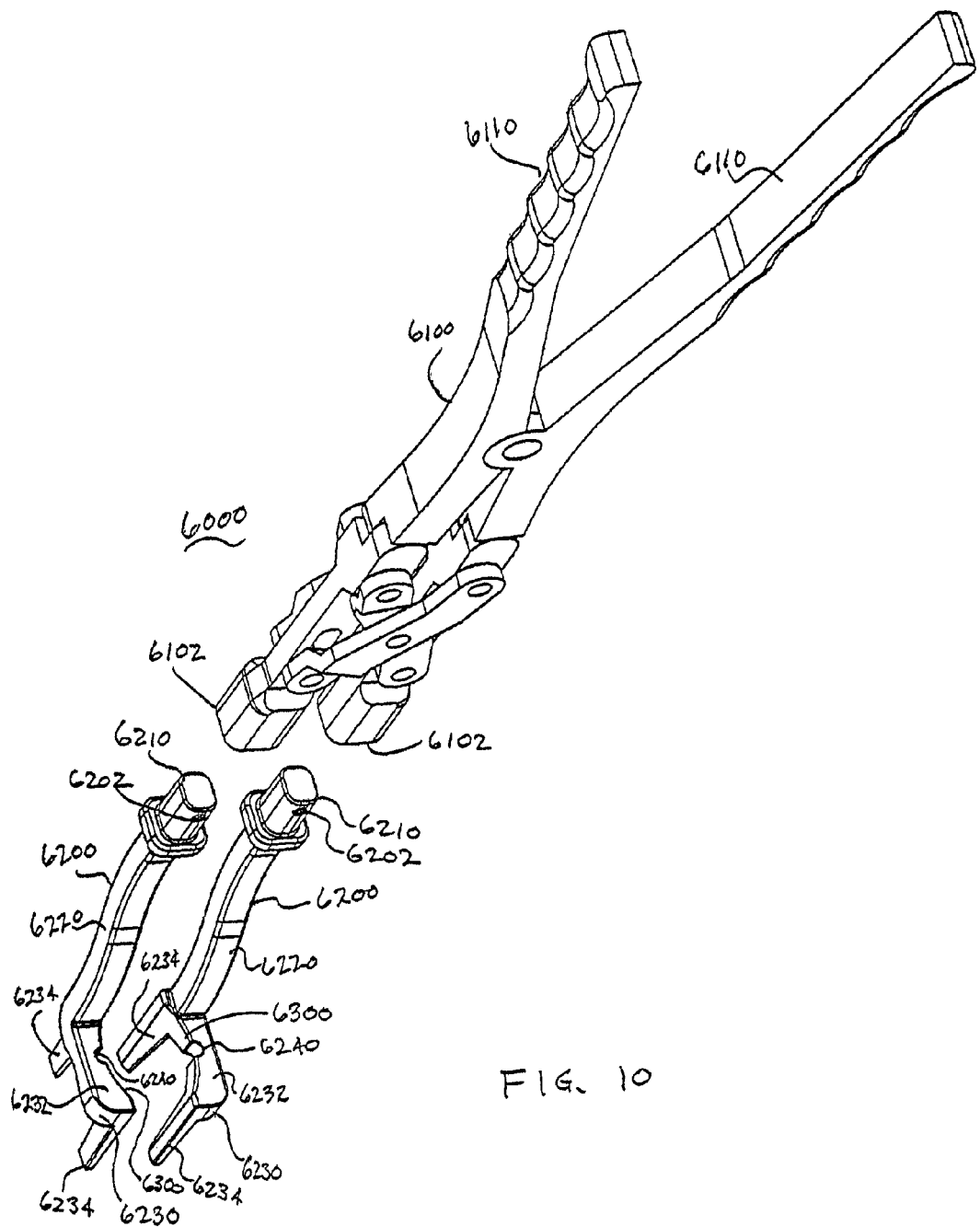
FIG. 10 shows a perspective view of a parallel insertion distractor of the present invention in disassembled form.
Figure 11:
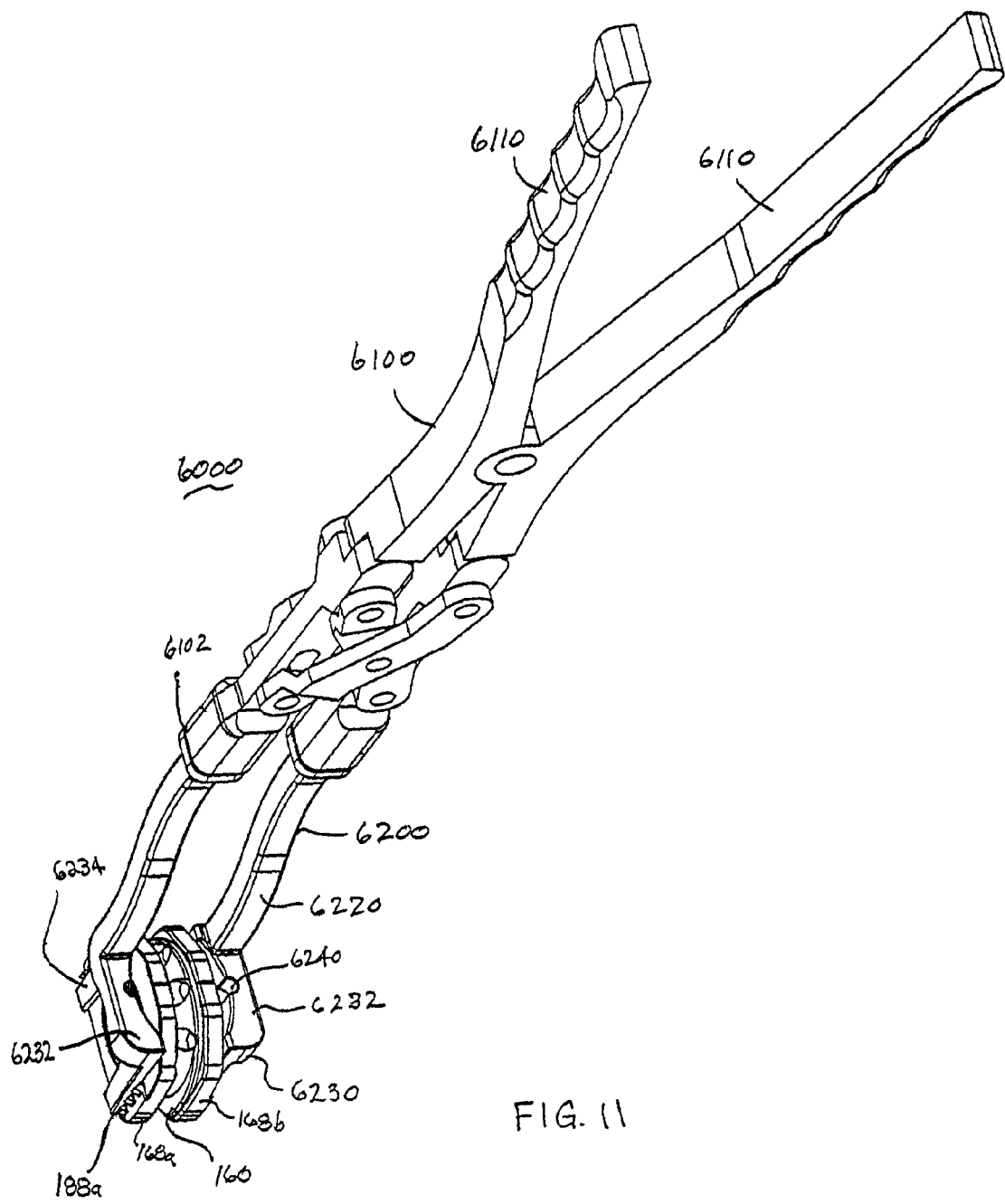
FIG. 11 shows a perspective view of a parallel insertion distractor of the present invention holding an exemplary artificial intervertebral disc.

Now referring to FIGS. 10 and 11, a preferred embodiment of a distractor 6000 is disclosed, comprising essentially a plying device 6100 such as but not limited to a Beere-style distractor and a pair of opposing forks 6200 adapted to engage therebetween an implant such as a disc 160.

Forks 6200 are adapted to connect to plying device 6100 using a fastening device such as but not limited to a floating ball bearing 6202 disposed on the proximal end 6210 of the fork 6200 to slidably and lockably engage a complementary portion 6102 of plying device 6100 such as but not limited to a channel, Preferably a male/female coupling arrangement is provided. Collar 6204 is preferably employed to provide a firm engagement between plying device 6100 and fork 6200.

Fork 6200 is preferably configured to engage the intervertebral space for distraction, while accommodating the passage of the disc 160 between the forks 6200 while the space is held in distraction. Accordingly, to facilitate such passage while the space is held in distraction, the forks 6200 are offset from the primary longitudinal axis of the plying device 6100, preferably as shown, such that the plying device can be operated to open the intervertebral space, but not obstruct a line of sight or an insertion of the disc 160 between the forks 6200 into the intervertebral space. More particularly, each fork 6200 comprises essentially an elongated portion 6220 terminating in a substantially U-shaped member 6230 comprising a base 6232 oriented substantially perpendicular to the elongated portion 6220 and a pair of laterally spaced tines 6234 oriented substantially perpendicular to the base 6232. With regard to the offset nature of the forks 6200, is it preferable that one of the tines 6234 be longitudinally aligned with the elongated portion 6220. It is further preferable that the base 6232 of the U-shaped member have a forward ridge surface perpendicular to the tines' outwardly facing surfaces, which ridge functions as a vertebral body stop to prevent the tines 6234 from being inserted too deeply into the intevertebral space.

With regard to the ability of the disc 160 to pass into the intervertebral space, the U-shaped member 6230 and tines 6234 are configured to engage with or avoid certain features of the disc 160 and/or an insertion tool (e.g., the inserter/impactor 4000). For example, the tines 6234 are preferably dimensioned to facilitate guidance and passage of the disc 160 into the intervertebral space, and out from the intervertebral space once the disc 160 is disposed therein. More particularly, the tines 6234 are dimensioned in width to slidably fit between the convex dome 184a, 184b and the teeth 188a, 188b on the disc 160 baseplates, and dimensioned in length to reach far enough into the intervertebral space to provide leverage support for the distraction. Also particularly, the U-shaped member 6230 of fork 6200 has an interior side (i.e., the side facing opposite fork 6200) defined by a notch 6240 and curved profile 6300, which notch allows passage of the vertebral body stops 4202 of the inserter/impactor 4000 as the disc 160 is inserted, and which curved profile permits passage of the convex dome 184a, 184b of the disc 160 as the disc is inserted.

In practice, the tines 6234 of forks 6200 of the distractor 6000 are placed in an intervertebral space far enough that the forward ridge surfaces of the base 6232 of the U-shaped member 6230 abut the anterior faces of the vertebral bodies. Next, the handles 6110 of plying device 6100 are squeezed together to separate the tine pairs to urge the vertebral bodies apart and create an aperture for passage of the disc 160 therethrough and into the intervertebral space. More particularly, in this position, the opposing interior sides of the U-shaped members 6230 of forks 6200, by virtue of facing curved profiles 6300, are positioned such that a disc 160, in a preferred embodiment already secured to the inserter/impactor 4000, is positionable and translatable between the U-shaped members 6230. The curved profiles 6300 accommodate the convex domes 184a, 184b of the disc 160. Notches 6240 accommodate vertebral body stops 4202 of the inserter/impactor 4000. The width of the tines 6234 accommodate the teeth 188a, 188b and convex dome 188a, 188b of baseplates 168a-b for passage and guidance along the tines 6234. Once the disc 160 is situated between the forks 6200, the inserter/impactor 4000 can be employed to manipulate the disc along the tines 6234. After insertion of the disc 160 in the intervertebral space, the distractor 600 is removed. and the inserter/impactor 4000 is disengaged from the disc 160. Further with regard to the configuration of the tines 6234, the tines' 6234 dimensions preferably facilitate removal of the tines 6234 as the forks 6200 are removed (i.e., the pulling out of the forks 6200 slides the tines 6234 between the convex dome 184a, 184b and the teeth 188a, 188b of the disc 160, to avoid damage to the disc 160 or the vertebral endplate. Further preferably, the thickness of the extent of the tines 6234 is higher than the height of the teeth 188a, 188b rising off the baseplate surfaces. Accordingly, the use of tines 6234 of at least this thickness avoids any possible damage to the vertebral endplates as a result of engagement of the endplate by the teeth 188a, 188b prior to full insertion of the disc 160. That is, using this insertion method, the teeth 188a, 188b do not engage the endplate until after the tines 6234 are removed (the thickness of the tines 6234 prevents the teeth 188a, 188b from engaging the endplates), which is once the disc 160 is properly placed, and therefore the initial engagement of the endplates by the teeth 188a, 188b is the final engagement. Accordingly, because no gouging or scratching of the endplates by the teeth 188a, 188b occurs, the teeth 188a, 188b are less likely to move from their engaged position, which provides a more secure foothold for the disc 160.

While there has been described and illustrated specific embodiments of instrumentation, it will be apparent to those skilled in the art that variations and modifications are possible without deviating from the broad spirit and principle of the invention. The invention, therefore, shall not be limited to the specific embodiments discussed herein.

The invention claimed is:

1. An instrument for distracting an intervertebral space, the instrument being adapted for use with an inserter having vertebral body stops for preventing overinsertion of an associated intervertebral disc into the intervertebral space, the instrument comprising:
    first and second elongated ramp members each having a first ramp portion including an interior surface with first and second laterally spaced grooves extending from a proximal end to a distal end thereof, and a second ramp portion extending distally from the first ramp portion, the second ramp portion including first and second laterally spaced prongs each having an interior surface and a groove extending from a proximal to a distal end thereof,
    wherein the first laterally spaced groove of the first elongate ramp is co-linear with the groove of the first prong and the second laterally spaced groove of the first elongate ramp is co-linear with the groove of the second prong,
    wherein the first and second elongated ramp members are connected at their proximal ends such that said interior surfaces face each other, the interior surfaces forming a passage dimensioned to accommodate the passage of an artificial intervertebral disc and a device for manipulating said disc, said passage effecting distraction of the intervertebral space,
    wherein at least one of said elongated ramp members further comprises longitudinal slot formed medially therethrough, the slot extending from the distal end towards the proximal end of said elongated ramp members, and
    wherein at least one of said elongated ramp members further comprises an exterior side having a ridge formed at the distal end of said elongated ramp members and disposed transversely to the longitudinal slot, the longitudinal slot extending through the ridge to allow vertebral body stops of the inserter to pass through the ridge.

2. The instrument according to claim 1, wherein each of said first and second elongated ramp members comprises a curved cross section.

3. An instrument for distracting an intervertebral space, the instrument being adapted for use with an inserter having vertebral body stops for preventing overinsertion of an associated intervertebral disc into the intervertebral space, the instrument comprising:
    first and second elongated ramp members each having an interior surface with first and second laterally spaced grooves extending from a proximal end to a distal end of the first and second elongated ramp members, and a first passage defined by the distal ends of each of the first and second elongated ramp members such that first and second laterally spaced prongs are formed adjacent the first passage at the distal end of each of the first and second elongated ramp members,
    wherein the first and second elongated ramp members are connected at their proximal ends such that said interior surfaces face each other, the interior surfaces forming a second passage dimensioned to accommodate the passage of an artificial intervertebral disc and a device for manipulating said disc, said second passage having a longitudinal axis perpendicular to longitudinal axis passing through said first passage at the distal end of each of the first and second elongated ramp members, and
    wherein at least one of the first and second elongated ramp members further comprises a slot having a longitudinal axis perpendicular to the longitudinal axis passing through the first passage at the distal end of the first and second elongated ramp members, and
    wherein at least one of said elongated ramp members further comprises an exterior side having a ridge formed at the distal end of said elongated ramp members and disposed transversely to the slot, the slot extending through the ridge to allow vertebral body stops of the inserter to pass through the ridge.

4. The instrument according to claim 3, wherein each of said first and second elongated ramp members comprises a curved cross section.

* * * * *